United States Patent [19]
Kowalyk et al.

[11] Patent Number: 5,554,029
[45] Date of Patent: Sep. 10, 1996

[54] DENTAL LASER APPARATUS AND METHOD FOR ABLATING NON-METALLIC DENTAL MATERIAL FROM A TOOTH

[75] Inventors: Kenneth Kowalyk; Michael J. Myers, both of Hilton Head Island, S.C.

[73] Assignee: Medical Laser Technology, Inc., Hilton Head Island, S.C.

[21] Appl. No.: 251,135

[22] Filed: May 31, 1994

[51] Int. Cl.$^6$ .............................. A61C 5/00; A61C 5/04; A61C 1/00; A61C 3/00
[52] U.S. Cl. ............................ 433/215; 433/226; 433/29
[58] Field of Search ...................... 433/29, 215

[56] References Cited

U.S. PATENT DOCUMENTS

| | | | |
|---|---|---|---|
| 3,769,963 | 11/1973 | Goldman et al. | |
| 4,521,194 | 6/1985 | Myers et al. | 433/215 |
| 4,818,230 | 4/1989 | Myers et al. | 433/215 |
| 4,874,315 | 10/1989 | Featherstone et al. | 433/215 |
| 4,940,411 | 7/1990 | Vassiliadis et al. | 433/215 |
| 4,951,663 | 8/1990 | L'Esperance, Jr. | 128/395 |
| 5,002,051 | 3/1991 | Dew et al. | 128/395 |
| 5,020,995 | 6/1991 | Levy | 433/215 |
| 5,055,048 | 10/1991 | Vassiliadis et al. | 433/215 |
| 5,059,191 | 10/1991 | Beyer et al. | 606/2 |
| 5,071,416 | 12/1991 | Heller et al. | 606/3 |
| 5,071,422 | 12/1991 | Watson et al. | 606/128 |
| 5,092,773 | 3/1992 | Levy | 433/224 |
| 5,092,864 | 3/1992 | Hayes et al. | 606/10 |
| 5,118,293 | 6/1992 | Levy | 433/215 |
| 5,122,060 | 6/1992 | Vassiliadis et al. | 433/215 |
| 5,123,845 | 6/1992 | Vassiliadis et al. | 433/215 |
| 5,151,029 | 9/1992 | Levy | 433/29 |
| 5,151,031 | 9/1992 | Levy | 433/226 |
| 5,169,318 | 12/1992 | Levy | 433/226 |
| 5,171,150 | 12/1992 | Levy | 433/226 |
| 5,180,304 | 1/1993 | Vassiliadis et al. | 433/215 X |
| 5,194,005 | 3/1993 | Levy | 433/215 |
| 5,207,576 | 5/1993 | Vassiliadis et al. | 433/215 |
| 5,228,852 | 7/1993 | Goldsmith et al. | 433/141 |
| 5,232,367 | 8/1993 | Vassiliadis et al. | 433/215 X |
| 5,257,935 | 11/1993 | Vassiliadis et al. | 433/215 |
| 5,267,856 | 12/1993 | Wolbarsht et al. | 433/215 X |
| 5,275,564 | 1/1994 | Vassiliadis et al. | 433/226 |
| 5,281,141 | 1/1994 | Kowalyk | 433/215 |
| 5,409,376 | 4/1995 | Murphy | 433/215 X |

FOREIGN PATENT DOCUMENTS

WO9011728  10/1990  Germany.

OTHER PUBLICATIONS

"Effect of Beam Absorptive Mediators On Acid Resistance of Surface Enamel By Nd–YAG Laser Irradiation," Toshio Morioka et al., Nov., 1982.
"The Use of a Laser For Debridement Of Incipient Caries," *The Journal of Prosthetic Dentistry*, Terry D. Myers et al., Jun., 1985.
The Select 1000 From U.S. Dental Laser, Inc.

*Primary Examiner*—Nicholas D. Lucchesi
*Attorney, Agent, or Firm*—Baker & Botts, L.L.P.

[57] ABSTRACT

A method of ablating non-metallic dental material from a tooth comprises the steps of generating radiation pulses having a predetermined wavelength, energy level, pulse repetition rate, and duration, and applying the radiation pulses to the non-metallic dental material in a tooth, whereby the non-metallic dental material is ablated from the tooth. The radiation may be generated by a frequency tripled Nd:YAG, an Er:YAG laser or an Er:YsGG laser and may have a wavelength of about 355 nanometers, 2.94 micrometers, and 2.79 micrometers respectively, for example.

9 Claims, 1 Drawing Sheet

DENTAL LASER APPARATUS AND METHOD FOR ABLATING NON-METALLIC DENTAL MATERIAL FROM A TOOTH

BACKGROUND OF THE INVENTION

Laser radiation techniques, generally, are known. Additionally, laser radiation equipment has been used in recent years in dentistry to replace certain mechanical dental tools which require the use of anesthetics to reduce the patient's sensitivity to pain. For example, U.S. Pat. No. 5,281,141 to Kowalyk discloses a method of removing tooth decay using a laser having an output wavelength which corresponds to the absorption band of a substance applied to the tooth decay.

Another example is disclosed in U.S. Pat. No. 5,194,005 to Levy. Levy discloses a method of applying laser radiation to a ceramic material to promote the growth of a crystal structure in that material and create a strong bond between the hydroxyapatite and the surrounding tooth material. Levy also discloses in U.S. Pat. No. 5,020,995 the use of a laser for removal of tooth and gum tissue at a wavelength of 1.06 micron together with a water/air mixture to control the thermal cutting action. In U.S. Pat. No. 5,151,029, Levy discloses use of a laser for removal or hardening of metal in a tooth. Various other patents address dental laser techniques.

Dentists have long used metal or dental amalgam materials to repair and protect teeth. Most of these materials, however, contain mercury. Further, because of the color and/or luster of the metals and amalgams, use of these materials in a visible portion of the mouth is generally cosmetically displeasing to many patients. Due to the poor cosmetics and concerns of potential mercury release associated with these metal and dental amalgam materials, there has been a recent movement in dentistry towards the use of non-metallic dental materials rather than metal or dental amalgam materials. For example, composite materials, which generally comprise microscopic particles of silica or quartz in a resin matrix, have been used more frequently in recent years. Also, the use of other non-metallic dental materials such as porcelain or ceramic restorations have been used as full crowns, inlays, and onlays in recent years.

These non-metallic dental materials, however, sometimes require removal. Due to differences in the coefficient of thermal expansion between the tooth and composite materials filled within a cavity in the tooth, for example, microscopic cracks may occur in the tooth. These cracks cause leakage in the tooth which may lead to pain and/or deterioration of the tooth. Also, non-metallic dental materials eventually wear during use due to the forces of mastication and have a tendency to stain over prolonged use. Therefore, when any of the above situations occur (or for other reasons), it is desirable for the non-metallic dental material to be fully or partially removed and replaced.

SUMMARY OF THE INVENTION

Accordingly, a need has arisen for an effective method of removing non-metallic dental material without requiring the use of anesthetics. Further, a need has arisen for a method of using laser radiation to ablate non-metallic dental material from a tooth without damaging the underlying tooth.

It is an object of the present invention to provide a method to safely ablate non-metallic dental material from a tooth using laser radiation.

More specifically, it is an object of the present invention to provide a method to remove composite, ceramic or porcelain materials from a tooth using laser radiation.

It is a further object to the invention to provide a dental laser method for removing materials from a tooth without excessive heating of the tooth, without the need for anesthetics and without pain or discomfort to the patient. It is also a goal of the invention to provide a method of ablation without the noise and vibration of the dental drill, handpiece or lung aspiration concerns of dental air-abrasives.

According to the above objects of the present invention, a method of ablating non-metallic dental material from a tooth comprises the steps of generating radiation pulses having a predetermined wavelength energy level, pulse repetition rate and duration, and applying the radiation pulses having predetermined characteristics to non-metallic dental material in a tooth, whereby the non-metallic dental material is ablated from the tooth. Preferably, a laser having a wavelength in the range of 100–600 nm or 2,000–4,000 nm is used because the composite resin or other non-metallic dental material has a relatively high absorption in those ranges. A frequency tripled Nd:YAG or an Er:YAG laser, which generates radiation having a wavelength of about 355 nanometers and 2.94 micrometers, respectively, may be used, for example. Preferably, the laser radiation pulses have a predetermined pulse repetition rate, average power, pulse duration and peak energy level.

Other objects and advantages of the present invention will become apparent to one of ordinary skill in the art upon review of the detailed description of the preferred embodiment.

DETAIL DESCRIPTION OF A PREFERRED EMBODIMENT

Figure 1:
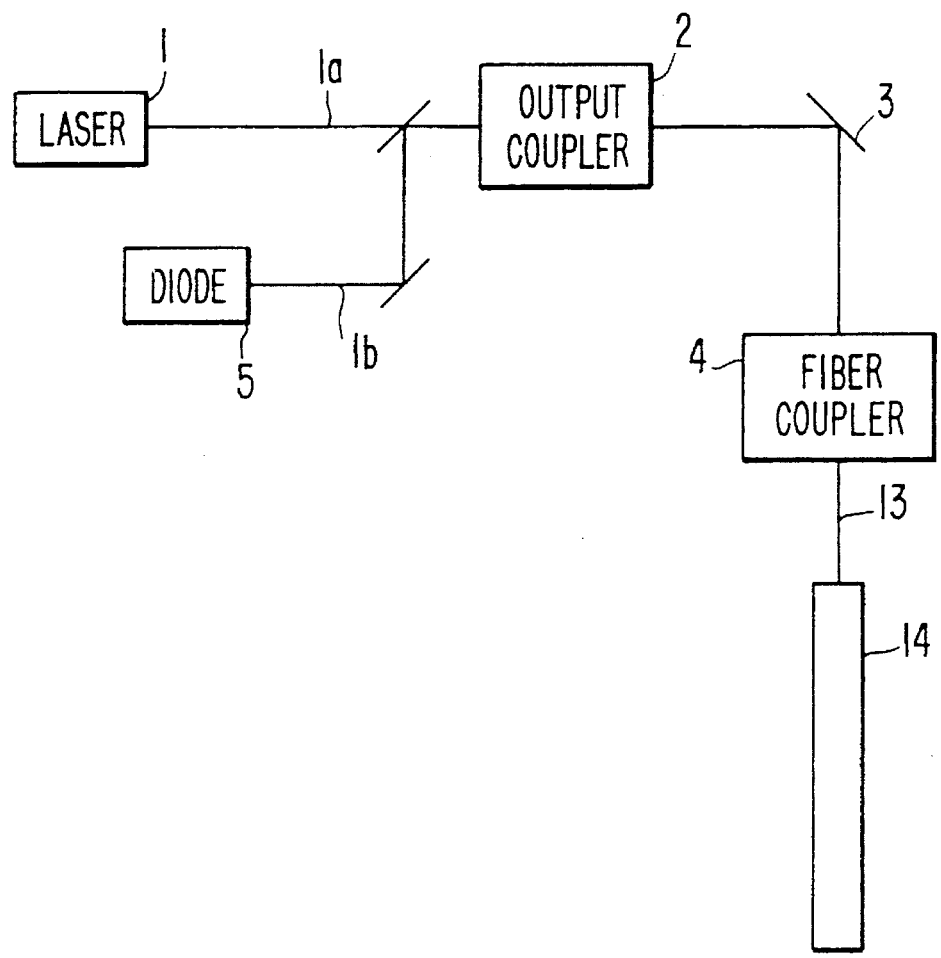
FIG. 1 depicts an apparatus for ablating non-metallic dental material from a tooth.
Figure 2:
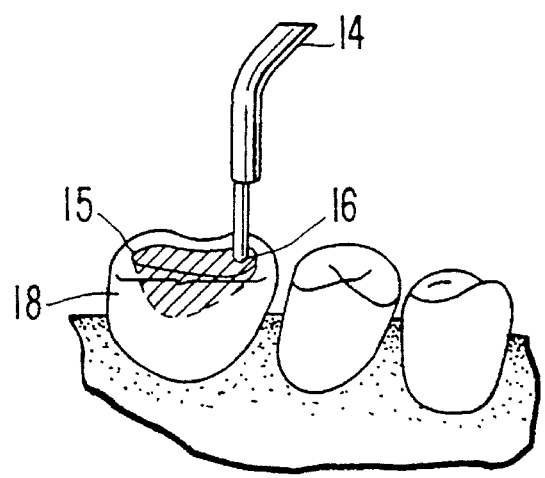
FIG. 2 depicts an apparatus according to the present invention ablating non-metallic dental material from a tooth.

With reference to FIGS. 1 and 2, a laser source 1 which is capable of producing a laser beam 1a, an output coupler 2 and a mirror 3 which reflects the beam to a fiber coupler 4 are disclosed. Optionally, the laser beam 1a may be joined by an aiming beam 1b, which may be produced by diode 5, and which may travel coaxially with the laser beam, in a known manner, along a fiber optic cable 13 to a commercially available laser handpiece 14. However, other delivery options and optical arrangements will be readily apparent and the invention is not limited to the described structure.

According to one method of the present invention, the laser beam generated has characteristics sufficient to ablate non-metallic dental material in a tooth but not damage the tooth tissue or other matter surrounding the material. Non-metallic dental materials may comprise composite material, ceramic, porcelain, and synthetic hydroxyapatite, for example. Composite materials typically comprise microscopic particles of silica or quartz in a resin matrix. When ablating composite materials, it may be desirable to only attack the resin matrix portion and thereby effectively ablate the composite material. The application of laser radiation using a fiber optic cable 13 applied using a commercially available laser handpiece 14, as depicted in FIG. 2, allows for the ablation of the non-metallic dental material.

Due to their chemical composition, commercially available dental restorative materials exhibit higher optical densities in the 100–600 nm and 2,000–4,000 nm wavelength range than natural tooth structure. Therefore, ablation using lasers generating radiation in these wavelength ranges may be performed without damaging surrounding natural tooth structure. Lasers generating radiation having a wavelength in this range are potentially more efficient in the ablation of these materials than traditional dental tools, at lower powers and less energy.

Laser source 1 may be, for example, an Nd:YAG laser (Neodymium, yttrium aluminum garnet). To ablate the non-metallic dental material, the frequency of the laser may be tripled or shifted via OPO or Raman techniques to generate wavelengths corresponding to the desired spectral range, for example. Other methods of laser wavelength modification may also be used to provide a desired laser radiation wavelength. The frequency tripled Nd:YAG laser may generate radiation pulses having a wavelength of about 355 nanometers, for example. The frequency tripled Nd:YAG laser may have a pulse repetition rate of between one and 10,000 pulses/sec, an average power of up to 100 watts, a pulse duration of between a pico second and several milliseconds, and a peak energy of up to five joules/pulse. For example, the frequency tripled Nd:YAG laser may be operated at a peak energy of about 20 milli-Joules having a pulse duration of about 30 nano-seconds, a frequency of about 20 Hz and provide an average power of about 400 milli-Watts. The frequency tripled Nd:YAG laser may also be Q-switched. These characteristics are determined by the ablation efficiency of the non-metallic dental materials. Low average powers with higher peak powers are preferred, so as not to cause pulpal damage in the tooth.

Another example of a suitable laser is the Er:YAG laser (erbium doped, yttrium aluminum garnet). This laser may generate radiation pulses having a wavelength of about 2.94 micrometers, for example. Another laser source that may be used is an Er:YSGG (erbium doped, yttrium scandium gallium garnet) laser generating radiation pulses having a wavelength of about 2.79 micrometers. The range for the pulse repetition rate, average power, pulse duration and energy of the Er:YAG and the Er:YSGG laser may also be similar to the frequency tripled Nd:YAG laser. For example, the Er:YSGG laser may be operated with a peak energy of about 250 milli-Joules, having a pulse duration of about 30 nano-seconds, a frequency of about 20 Hz and providing an average power of 400 milli-Watts.

Other lasers may also be used having similar ranges of operation. Lasers such as the Argon laser (514), doubled Nd:GSGG (1061–530 nm), Nd:YV04 (1064–532 nm), Nd:KGW (1060–530 nm), Nd:Phosphate glass (1053–526 nm), Nd:YAP (1080–540 nm), Nd:GGG/GSGG (1064–532 nm),Nd:YLP (1053–526 nm+1047–523 nm), Nd:YALO/YAP (1080–540 nm), Cr:Fosterite (1235–617 nm), Alexandrite (755–377 nm), Nd:GdV04 (1060–530 nm), Ti:Sapphire (800–400 nm), Cr:LiSAF/LiCAF (840–420 nm), and Nd:Silicate glass (1062–531 nm), for example, may be used. Some of these other laser materials are tunable within various output wavelength regions near those values indicated above.

The method of ablating non-metallic dental material generally comprises using laser source 1 to generate laser radiation pulses. These laser radiation pulses are applied through output coupler 2, fiber coupler 4, and a fiber optic cable 13 to a commercially available laser handpiece 14. This handpiece may comprise a tip 16 comprising a optical fiber which is connected to fiber optic cable 13 and therefore receives and transmits the laser radiation pulses generated by laser source 1. Tip 16 then may be applied to the composite material 15 in a tooth 18. The laser radiation thus ablates composite material 15, but due to the selected wavelength leaves unharmed the tooth tissue of tooth 18 underlying composite material 15 because of the wavelength of the radiation applied thereto. Composite material 15 may also be ceramic, porcelain, or any other type of non-metallic dental material, for example.

Flushing of ablated material using air and/or water or other fluids and gases such as fluorocarbons and nitrogen, for example, may be used to remove the ablated material from the area where the radiation pulses are being applied. This increases efficiency by avoiding the situation where lasing of the ablated particles occurs. Depending on the laser used and its frequency (and other characteristics) one type of fluid may be preferred over another. For example a fine spray of water and air may be used to flush away the ablated material when using the Er:YSGG and Er:YAG lasers. A simultaneous jet of air may be used to remove ablated material when using the frequency tripled Nd:YAG laser, however, the invention is not so limited. The type and amount of fluid and/or gas used is determined based on the inherent photophysical properties encountered with the laser/material interaction.

The foregoing is a description of an embodiment of the present invention. The invention is not limited to the foregoing description, but rather, is to be limited only by the claims appended hereto. Numerous variations and modification will be apparent to one of ordinary skill in the art within the scope of the invention.

What is claimed is:

1. A method of ablating a non-metallic dental material from a tooth comprising the steps of:

generating radiation pulses having a predetermined wavelength, energy level, pulse repetition rate and duration; and applying the radiation pulses to the non-metallic dental material in a tooth;

whereby the non-metallic dental material is ablated from the tooth;

wherein the non-metallic dental material comprises a composite material having a resin component and whereby the radiation pulses ablate substantially only the resin component.

2. The method of claim 1, wherein the radiation pulses are generated by a frequency tripled Nd:YAG laser having a wavelength of about 355 nanometers.

3. The method of claim 1, wherein the radiation pulses are generated by an Er:YSGG laser generating radiation pulses having a wavelength of about 2.79 micrometers.

4. The method of claim 1, wherein the radiation pulses are generated by an Er:YAG laser generating radiation pulses having a wavelength of about 2.94 micrometers.

5. The method of claim 1 further comprising the step of flushing ablated non-metallic material.

6. A method of ablating a non-metallic dental material from a tooth comprising the steps of:

providing an optical fiber having an input end and an output end;

applying the output end of said optical fiber to the non-metallic dental material in a tooth; and generating radiation pulses on the input end of the optical fiber;

whereby the radiation pulses are applied to the non-metallic dental material through the optical fiber and ablate the non-metallic dental material in the tooth wherein the non-metallic dental material comprises a composite material having a resin component and whereby the radiation pulses ablate substantially only the resin component.

7. The method of claim 6, wherein the radiation pulses are generated by a frequency tripled Nd:YAG laser.

8. The method of claim 6, wherein the radiation pulses are generated by an Er:YAG laser.

9. The method of claim 6, wherein the radiation pulses are generated by an Er:YSGG laser.

* * * * *